United States Patent [19]

O'Reilly et al.

[11] Patent Number: 4,935,541

[45] Date of Patent: Jun. 19, 1990

[54] PREPARATION OF 2,4,5-TRIFLUOROBENZOIC ACID BY DECARBOXYLATION OF 3,4,6-TRIFLUOROPHTHALIC ANHYDRIDE

[75] Inventors: Neil J. O'Reilly, Grand Island; William S. Derwin, Buffalo; Henry C. Lin, Gr. Island, all of N.Y.

[73] Assignee: Occidental Chemical Corporation, Niagara Falls, N.Y.

[21] Appl. No.: 439,230

[22] Filed: Nov. 20, 1989

[51] Int. Cl.$^5$ ............................................... C07C 51/38
[52] U.S. Cl. .................................................... 562/479
[58] Field of Search ........................................ 560/479

[56] References Cited

U.S. PATENT DOCUMENTS 4,769,492  9/1988  Kaieda et al. .................... 500/479
4,782,180  11/1988  Wemple ............................ 500/479

FOREIGN PATENT DOCUMENTS 115040   9/1988  European Pat. Off. .
3420796  12/1985  Fed. Rep. of Germany .
3631906  3/1988  Fed. Rep. of Germany .
052737   2/1989  Japan .
160944   6/1989  Japan .
318934   7/1989  Japan .

OTHER PUBLICATIONS

Bridges, A. et al., J. Org. Chem., 55(2), 773–775, 1990.

Primary Examiner—Paul J. Killos
Attorney, Agent, or Firm—James F. Tao; John H. Englemann

[57] ABSTRACT

It has been discovered that 3,4,6-trifluorophthalic anhydride may be decarboxylated by heating in a polar aprotic solvent to yield 2,4,5-trifluorobenzoic acid.

11 Claims, No Drawings

PREPARATION OF 2,4,5-TRIFLUOROBENZOIC ACID BY DECARBOXYLATION OF 3,4,6-TRIFLUOROPHTHALIC ANHYDRIDE

BACKGROUND OF THE INVENTION

This invention relates to a method for the preparation of 2,4,5-trifluorobenzoic acid by the decarboxylation of 3,4,6-trifluorophthalic anhydride. 2,4,5-trifluorobenzoic acid is a useful intermediate in the manufacture of quinolone antibacterial drugs. Heretofore, 2,4,5-trifluorobenzoic acid has been difficult to synthesize. One known method of synthesis involves the cyanation of 2,4,5-trifluorobromobenzene using copper cyanide in dimethyl formamide, followed by hydrolysis of the product nitrile with sulfuric acid [Sanchez, J. P. et al *J. Med. Chem.* (1988), 31, 983]. This synthetic method is difficult to use, and expensive.

We have now discovered that 2,4,5-trifluorobenzoic acid may be prepared by the decarboxylation of 3,4,6-trifluorophthalic anhydride. The reaction may be conducted in dipolar aprotic solvents, without the use of a catalyst. However, the use of a catalyst such as copper, a copper oxide, or a copper salt is preferred. Surprisingly, one of the two carboxyl groups is removed to a greater extent, and 2,4,5-trifluorobenzoic acid is produced in good yield. 3,4,6-trifluorophthalic acid may be prepared from 3,4,6-trichlorophthalic acid. The acid is reacted with aniline to form 3,4,6-N-phenylphthalimide. The phthalimide is then treated with potassium fluoride in sulfolane using tributylhexadecylphosphonium bromide as a phase transfer catalyst. The method is disclosed in copending patent application Ser. No. 07/315,748, which is hereby specifically incorporated by reference. The resulting 3,4,6-trifluorophthalic acid may be readily converted to the corresponding anhydride by heating the acid with mixed xylenes and removing the water as an azeotrope.

Many examples of decarboxylation reactions have been reported. Basic substances have been used to catalyze such reactions. For example, it is disclosed in O. S. Tarbell, et al Org. Syn., III coll. vol. (1955) 267, that 3,5-dichloro-4-hydroxybenzoic acid may be decarboxylated by vigorous heating in N,N-dimethylaniline. It is disclosed in A. Singer and S. M. McElvane, Org. Syn., coll. vol. II (1943) 214, that 3,5-dicarboxy-2,6-dimethylpyridine di-potassium salt may be completely decarboxylated by heating the salt in the presence of calcium hydroxide. Copper and copper salts have been used to catalyze decarboxylation reactions. For example, H. R. Snyder et al, Org. Syn., coll. vol. III (1955) 471 disclose the use of copper oxide catalyst for the decarboxylation of imidazole-4,5-dicarboxylic acid.

Some compounds may be decarboxylated without catalysts. For example, C. Wang, Bul. Inst. Kim. Acad. Sinica, no. 2156 (1972), as abstracted in CA79 (15):91729, discloses that tetrachloro or tetrabromophthalic acids, or their anhydrides, may be decarboxylated to the corresponding benzoic acids when refluxed in dimethyl formamide. 3-nitrophthalic acid underwent a similar reaction.

Decarboxylation is not always a predictable reaction. For example, A. S. Sultanov, J. Gen. Chem. (USSR) 16 1835 (1946) as abstracted in CA 41:6223(e) discloses that salicylic acid may be decarboxylated by autoclaving the acid in the presence of copper bronze and benzene at 170° C. The acid alone decarboxylates at 205° C. while in the presence of aniline decarboxylation begins at 170° C. In the case of salicylic acid, aniline and copper bronze seem to be equal in catalytic ability. On the other hand, when phthalic acid is heated in aniline at 180° C., decarboxylation does not occur and instead phthalic anhydride is produced. Heating phthalic anhydride with copper bronze in chloroform at 180° C. gave a 22% yield of benzoic acid. Phthalic acid was found to decarboxylate to yield benzoic acid merely by heating in water at 235° C.

Decarboxylations of certain fluorophthalic acids have been reported.

3,4,5,6-tetrafluorophthalic acid decarboxylates under certain conditions to yield 2,3,4,5-tetrafluorobenzoic acid. For example, Japanese Patent JP 61/85349 A2[86/85349] as abstracted in CA105:152719r discloses that the reaction may be conducted in an aqueous medium at 150° to 230° C. The reaction may be carried out at a lower temperature (100° to 250° C.) in the presence of copper, zinc, cadmium, iron, cobalt, nickel, other oxides, hydroxides and/or carbonates. Japanese Patent Application 86/103,317 as abstracted in CA105 (22):193368u discloses that the above reaction may be conducted in an aqueous medium at a pH of 0.7–2.2 at a temperature of 100°–200° C. The pH of the medium is adjusted by acidifying with sulfuric acid and partial neutralization with calcium hydroxide. Japanese Patent No. 63/295529m A2[88/295529] (as abstracted in Chem. Abstracts CA 111 (3): 23221X) discloses that the reaction may be conducted at 130° in tri-butylamine.

Yacobsen, O. J. discloses in Zh. Obsch. Khim. 36 (1966) page 139 (as appearing in Journal of General Chemistry of the U.S.S.R., translated from Russian, 36 (1966) page 144), that tetrafluorophthalic acid may be decarboxylated to yield 2,3,4,5-tetrafluorobenzoic acid by heating for one hour at 145° C. in dimethyl formamide.

Under slightly more vigorous conditions, Japanese Patent Application 61/43130 A2[86/43130] as abstracted in CA106 (1):46295 discloses that 3,4,5,6-tetrafluorophthalic acid may be completely decarboxylated to 1,2,3,4-tetrafluorobenzene. The conditions for complete decarboxylation are an aqueous medium from 210° to 300° C. with the optional presence of a catalyst.

Japanese Patent Application No. 86/290399 as abstracted in CA109 (19) 170038e discloses that 3,5,6-trifluoro-4-hydroxyphthalic acid may be decarboxylated by heating the compound for three hours, in water, under nitrogen atmosphere, at 140° C. (in a sealed tube) to yield 2,4,5-trifluoro-3-hydroxybenzoic acid.

Aroskar et al (J. Chem. Soc. (1964) 2975) discloses a method for preparing 3,4,6-trifluorophthalic acid. They found that upon slowly heating a mixture of the acid and soda lime to 300° C., they obtained a low yield of the fully decarboxylated 1,2,4-trifluorobenzene.

Japanese Patent No. JP 01/52737 discloses the preparation of 2,4,5-trifluorobenzoic acid by the decarboxylation of 3,4,6-trifluorophthalic acid in a liquid medium at a temperature of 80°–250° C. The liquid media disclosed include water, DMSO, tetramethylsulfone, DMF, dimethylacetamide, N-methylpyrrolidone, acetonitrile, nitrobenzene, diethylene glycol, dimethyl ether, tetraethylene glycol, dimethyl ether, and tertiary amines such as tributyl amine, and dimethyl aniline. The patent further discloses that a catalyst such as the ammonium or alkaline earth metal salts of hydroxide, carbonate, bicarbonate, sulfate or fluoride may be used.

DETAILED DESCRIPTION OF THE INVENTION

It has been discovered that 3,4,6-trifluorophthalic anhydride may be decarboxylated in a polar aprotic solvent to yield 2,4,5-trifluorobenzoic acid.

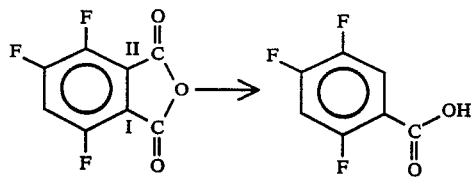

The decarboxylation process is not complex. The anhydride is dissolved in the appropriate solvent and the mixture is heated, along with stirring, until the desired percentage of starting material has been converted to products. At any point in the reaction, the degree of conversion of starting material to products can readily be judged by gas chromatographic analysis. However, the reaction is reproducible and once conditions, within the scope of this invention, have been established for conducting the reaction, the gas chromatographic analysis need not be conducted routinely. The desired product of this reaction is 2,4,5-trifluorobenzoic acid. However, it can readily be seen that the 2 carboxyl groups in the 3,4,6-trifluorophthalic anhydride molecule are not equivalent to each other. The removal of the carboxyl position at II leads to the desired product, while the removal of the carboxyl at position I leads to 2,3,5-trifluorobenzoic acid. The 2,3,5 product is not desired and the methods of this invention minimize its formation.

In this case, it has been found that a dipolar aprotic solvent such as dimethyl formamide, dimethyl acetamide, dimethyl sulfoxide, sulfolane and N-methylpyrrolidone is appropriate for running the decarboxylation reaction. The preferred solvents are dimethyl sulfoxide and N-methylpyrrolidone, and the most preferred solvent is N-methylpyrrolidone.

Although the reaction occurs without a catalyst, it tends to be rather slow. The use of a catalyst such as metallic copper, $Cu_2O$, CuO, or copper salts such as CuCl, CuBr or CuI is preferred in order to conduct the reaction in a reasonable period of time. The decarboxylation reaction may be conducted at temperatures ranging from about 125°–175° C. The preferred temperature is about 150° C. The 2,4,5-trifluorobenzoic acid produced by this reaction may be purified, if desired, by standard methods such as column chromatography or recrystallization.

The following specific examples are provided to further illustrate this invention and the manner in which it may be carried out. It will be understood, however, that the specific details given in the examples have been chosen for purposes of illustration and are not to be construed as a limitation on the inveniton. In the examples, unless otherwise indicated, all parts and percentages are by weight and all temperatures are in degrees Celsius.

EXAMPLE 1

Preparation of 3,4,6-Trifluorophthalic Anhydride From 3,4,6-Trifluorophthalic Acid A 25 mL round-bottom flask equipped with a Barrett trap and a condenser was charged with 1.00 g of 3,4,6-trifluorophthalic acid and 15 mL of mixed xylenes under a dry nitrogen atmosphere. The reaction mixture was then heated under reflux with azeotropic removal of water for 5 hr. and was then cooled to room temperature. After the addition of 20 mL of hexane the mixture was cooled in an ice bath. The solvent was then removed on a rotary evaporator to afford 3,4,6-trifluorophthalic anhydride.

EXAMPLE 2

Decarboxylation of 3,4-6-Trifluorophthalic Anhydride in DMAc in the Absence of Catalyst A 5 mL round-bottomed flask equipped with a reflux condenser, a magnetic stirrer and a dry nitrogen atmosphere was charged with 0.08 g of 3,4,6-trifluorophthalic anhydride and 1 mL of DMAc. The reaction mixture was heated with stirring for 23 hr. at 150° C. and then analyzed by GC to contain 25.3% of 2,4,5-trifluorobenzoic acid, 18.7% of the starting 3,4,6-trifluorophthalic anhydride, and 55.9% of a by-product believed to be 3,6-difluoro-4-dimethylamino-phthalic anhydride.

EXAMPLE 3

Decarboxylation of 3,4-6-Trifluorophthalic Anhydride in DMAc in the Presence of Cuprous Oxide A 5 mL round-bottomed flask equipped with a reflux condenser, a magnetic stirrer and a dry nitrogen atmosphere was charged with 0.2 g of 3,4,6-trifluorophthalic anhydride, 0.02 g of $Cu_2O$, and 2 mL of DMAc. The reaction mixture was heated with stirring for 12 hr. at 103°–126° C. and then analyzed by GC to contain 57% of 2,4,5-trifluorobenzoic acid and 34% of 2,3,5-trifluorobenzoic acid.

We claim:

1. A process for the preparation of 2,4,5-trifluorobenzoic acid which comprises dissolving 3,4,6-trifluorophthalic anhydride in a dipolar aprotic solvent, and heating said solution until said 3,4,6-trifluorophthalic anhydride has been consumed.

2. A process according to claim 1 wherein said solvent is dimethyl sulfoxide and the reaction is conducted at a temperature between 125° and 175° C.

3. A process according to claim 1 wherein said solvent is dimethyl acetamide and the reaction is conducted at a temperature between 125° and 175° C.

4. A process according to claim 1 wherein said solvent is N-methylpyrrolidone and the reaction is conducted at a temperature between 125° and 175° C.

5. A process according to claim 1 wherein said solvent is sulfolane and the reaction is conducted at a temperature between 125° and 175° C.

6. A process for the preparation of 2,4,5-trifluorobenzoic acid which comprises dissolving 3,4,6-trifluorophthalic anhydride in a dipolar aprotic solvent, adding thereto a catalytically effective amount of a catalyst selected from the group consisting of Cu, $Cu_2O$, $CuF_2$, $CuCl_2$, CuBr, CuI and $CuBr_2$, and heating said solution until said 3,4,6-trifluorophthalic anhydride has been consumed.

7. A process according to claim 6 wherein said catalyst is $Cu_2O$.

8. A process according to claim 7 wherein said solvent is dimethyl sulfoxide and the reaction is conducted at a temperature between 125° and 175° C.

9. A process according to claim 7 wherein said solvent is dimethyl acetamide and the reaction is conducted at a temperature between 125° and 175° C.

10. A process according to claim 7 wherein said solvent is N-methylpyrrolidone and the reaction is conducted at a temperature between 125° and 175° C.

11. A process according to claim 7 wherein said solvent is sulfolane and the reaction is conducted at a temperature between 125° and 175° C.

* * * * *

UNITED STATES PATENT OFFICE
CERTIFICATE OF CORRECTION

PATENT NO. : 4,935,541

DATED : Jun. 19, 1990

INVENTOR(S) : O'Reilly et al.

It is certified that error appears in the above-identified patent and that said Letters Patent is hereby corrected as shown below:

In Column 1, line 34, correct Ser. No. 07/315,748 to 07/315,746,

Signed and Sealed this

Seventeenth Day of September, 1991

Attest:

HARRY F. MANBECK, JR.

*Attesting Officer*    *Commissioner of Patents and Trademarks*